United States Patent
Chang et al.

(10) Patent No.: US 10,935,533 B2
(45) Date of Patent: Mar. 2, 2021

(54) METHOD OF ASSEMBLING A FUGITIVE GAS SENSOR ENCLOSURE

(71) Applicant: International Business Machines Corporation, Armonk, NY (US)

(72) Inventors: Josephine B Chang, Ellicott City, MD (US); Yves Martin, Ossining, NY (US); Theodore G. Van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 378 days.

(21) Appl. No.: 15/869,641

(22) Filed: Jan. 12, 2018

(65) Prior Publication Data

US 2019/0219554 A1   Jul. 18, 2019

(51) Int. Cl.
*G01R 3/00* (2006.01)
*G01N 33/00* (2006.01)
*G01M 3/04* (2006.01)

(52) U.S. Cl.
CPC ..... *G01N 33/0073* (2013.01); *G01N 33/0011* (2013.01); *G01M 3/04* (2013.01); *G01N 33/0047* (2013.01)

(58) Field of Classification Search
CPC ........... G01N 33/0011; G01N 33/0047; G01N 33/0073; G01M 3/04
See application file for complete search history.

(56) References Cited

U.S. PATENT DOCUMENTS

| | | | |
|---|---|---|---|
| 3,989,614 A | 11/1976 | Tien | |
| 6,453,723 B1 | 9/2002 | Ichikawa et al. | |
| 6,453,726 B1 | 9/2002 | Gutierrez et al. | |
| 6,824,661 B2 | 11/2004 | Lawless | |
| 7,168,295 B2 | 1/2007 | Yamauchi et al. | |
| 7,371,092 B2 | 5/2008 | Okumura et al. | |
| 7,559,229 B2 | 7/2009 | Yamada | |
| 8,552,874 B2 | 10/2013 | Wander et al. | |
| 8,816,867 B2 | 8/2014 | Mammoto et al. | |
| 8,915,121 B2 | 12/2014 | Kumar et al. | |
| 10,466,174 B2 * | 11/2019 | Glacer | G01N 21/1702 |
| 10,613,023 B1 * | 4/2020 | Martin | G01N 21/1717 |

FOREIGN PATENT DOCUMENTS

WO    2015038165 A1    3/2015

OTHER PUBLICATIONS

Grainger Industrial Supply "allegro remote co alarm", Retrieved online URL:<https://www.grainger.com/product/ALLEGRO-Remote-CO-Alarm3WYV7?s_pp=false&picUrl=//static.grainger.com/rp/s/is/image/Grainger/3WYV7_AS03?$smthumb$>; downloaded Jan. 12, 2018; 1 pg.
Thorne & Derrick International "Crowson XGard", Retrieved online URL:<http://thorneandderrick.com/product/crowcon-xgard/>, dated Jul. 2015; 2 pages.

* cited by examiner

*Primary Examiner* — Paul D Kim
(74) *Attorney, Agent, or Firm* — Cantor Colburn LLP; Joseph Petrokaitis

(57) ABSTRACT

A gas sensor enclosure is provided. The gas sensor enclosure includes at least two coaxial shells, a gas sensor, a gas permeable membrane that exposes a portion of the gas sensor to gas exchange through one of the at least two coaxial shells and a screen. The screen encloses the at least two coaxial shells, the gas sensor and the gas permeable membrane.

8 Claims, 4 Drawing Sheets

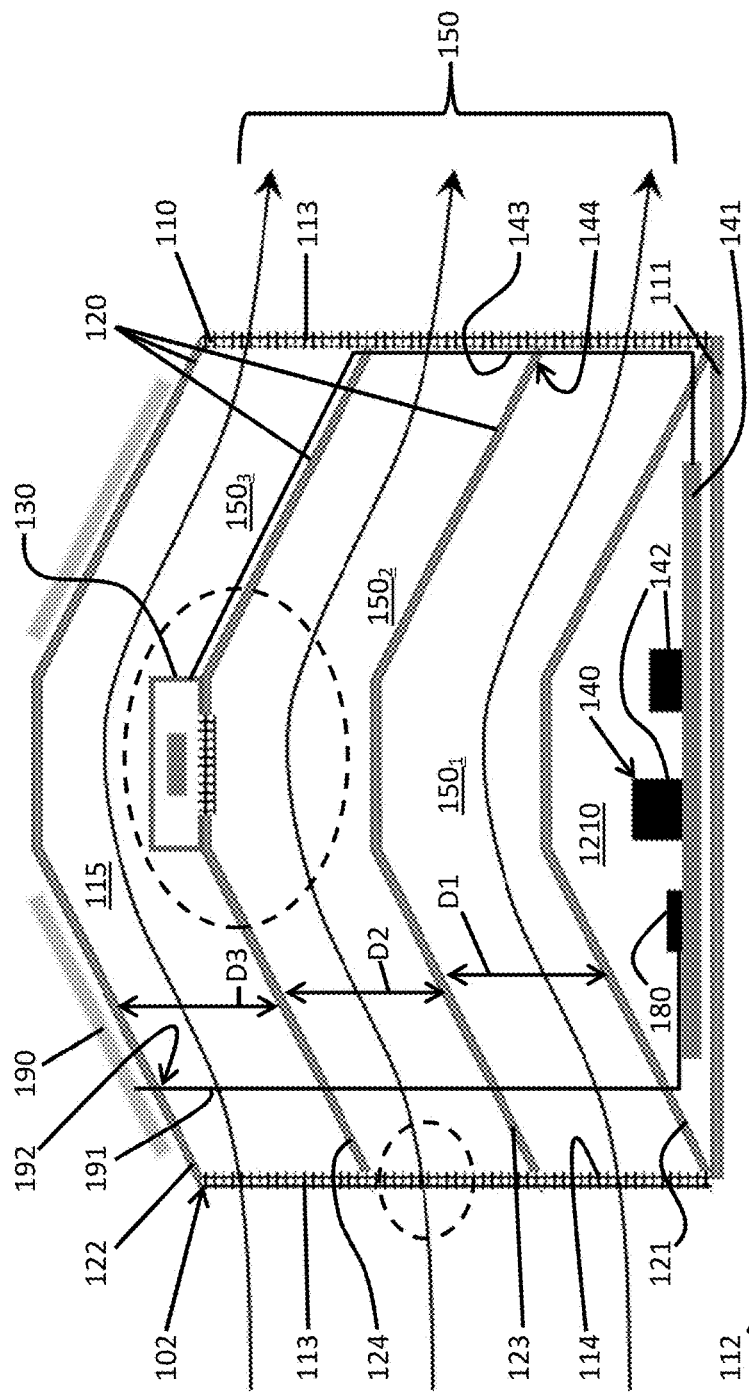
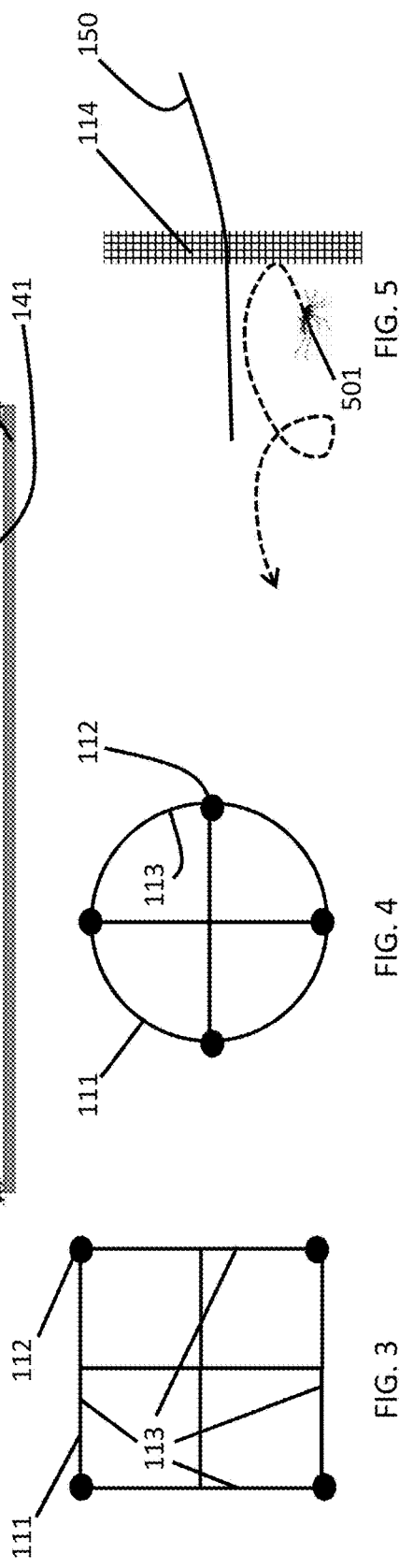

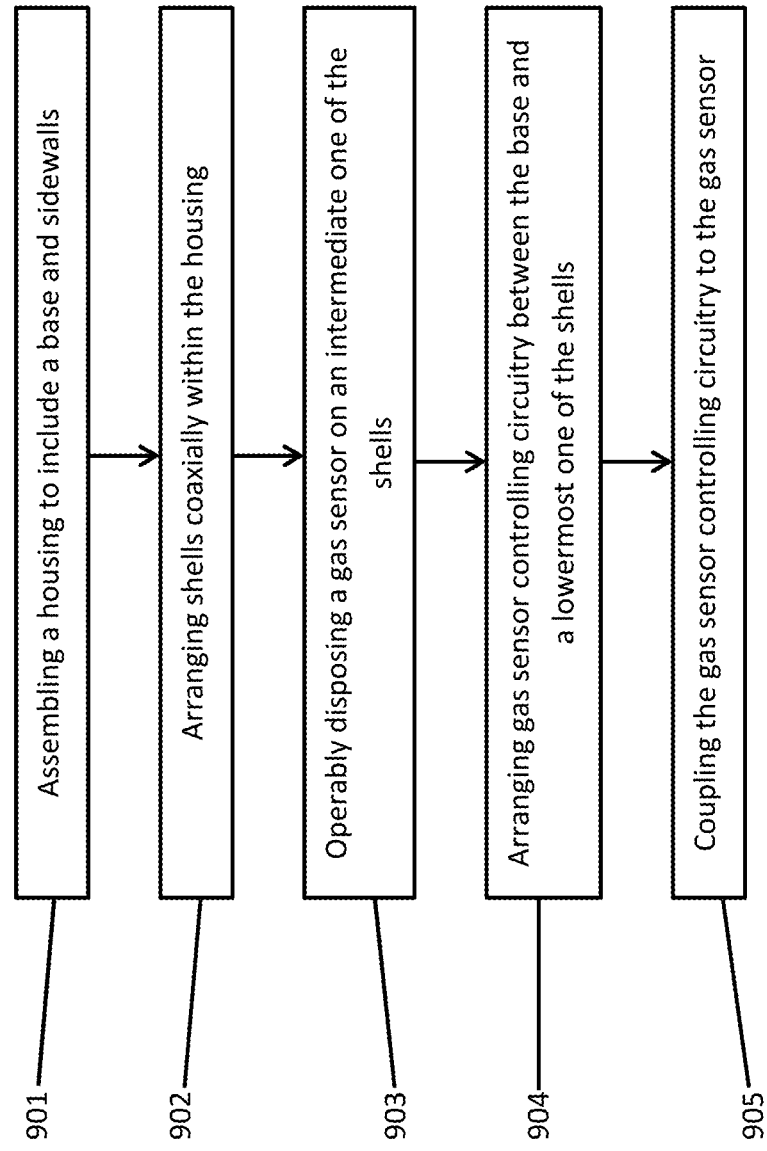

METHOD OF ASSEMBLING A FUGITIVE GAS SENSOR ENCLOSURE

STATEMENT REGARDING FEDERALLY SPONSORED RESEARCH OR DEVELOPMENT

This invention was made with Government support under DE-AR0000540 awarded by Department of Energy. The Government has certain rights to this invention.

BACKGROUND

The present invention relates in general to gas sensing. More particularly, the present invention relates to a fugitive gas sensing enclosure with a short integration time.

Fugitive gas emissions are the unintended emission of gases or vapors from pressurized equipment due to, for example, leaks or other compromises in the equipment. The ability to sense fugitive gases is growing in importance. Methane sensing in particular is an emergent capability that has high priority. This is due in many cases to the increased amount of hydro-fracking that is currently being used to extract methane, the leakage associated with such fracking operations, and the implications for global warming. Further, combustible gas sensing has always been of interest in urban areas to avoid fires and explosions.

SUMMARY

Embodiments of the invention are directed to a gas sensor enclosure. A non-limiting example of the gas sensor enclosure includes at least two coaxial shells, a gas sensor, a gas permeable membrane that exposes a portion of the gas sensor to gas exchange through one of the at least two coaxial shells and a screen. The screen encloses the at least two coaxial shells, the gas sensor and the gas permeable membrane.

Embodiments of the invention are directed to a gas sensor enclosure. A non-limiting example of the gas sensor enclosure includes a base, screens extending upwardly from the base, and lower and upper shells enclosed by the screens above the base. The upper shell includes a gas permeable membrane. The gas sensing enclosure further includes a gas sensor operably disposed on the upper shell adjacent to the gas permeable membrane and circuitry. The circuitry is arranged between the base and the lower shell and is configured to control operations of the gas sensor.

Embodiments of the invention are directed to a method of assembling a gas sensor enclosure. A non-limiting example of the method includes assembling a housing to include a base and sidewalls extending upwardly from the base. The sidewalls include gas and fluid permeable but insect impermeable screens. The method further includes arranging shells coaxially within the housing. The shells include a lowermost shell, an uppermost shell and an intermediate shell between the lowermost and uppermost shells. The intermediate shell includes a gas permeable membrane. In addition, the method includes operably disposing a gas sensor on the intermediate shell adjacent to the gas permeable membrane and arranging gas sensor controlling circuitry between the base and the lowermost shell. Finally, the method includes coupling the gas sensor controlling circuitry to the gas sensor via through-holes in the lowermost and intermediate shells.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 2 is a side view of a gas sensor enclosure in accordance with embodiments of the invention;

FIG. 3 is a top down view of the gas sensor enclosure of FIG. 2 in accordance with embodiments of the invention;

FIG. 4 is a top down view of the gas sensor enclosure of FIG. 2 in accordance with alterative embodiments of the invention.

FIG. 5 is an enlarged side view of the smaller encircled portion of the gas sensor enclosure of FIG. 2;

FIG. 9 depicts a method of assembly a gas sensor enclosure in accordance with embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Turning now to an overview of technologies that are more specifically relevant to aspects of the invention, remote monitoring of fugitive gases in given locations over extended periods is becoming increasingly important. Such monitoring will require that monitoring devices be deployed. These monitoring devices will need to have low power modalities and be rugged. That is, the monitoring devices will need to be able to operate in an exterior environment that is exposed to the elements, insects, small animals, and potentially corrosive media from human operations among other sources.

Turning now to an overview of the aspects of the invention, one or more embodiments of the invention address the need for low power and rugged monitoring devices by providing for a package or enclosure for a low power autonomous sensor. This low power autonomous sensor is rugged and operable in, for example, an outdoor environment. The package or enclosure includes a coaxial stack of shells, protective membranes and sheathing that are built around a gas permeable membrane and a gas sensor. These features are configured and combined together in a novel way to provide a gas permeable sensor enclosure, exclude particulates from the gas permeable membrane and the gas sensor, constrain airflow over an area of the gas sensor, exclude insect activity, protect the sensor and electronics within the enclosure from direct solar heating, exclude rain and moisture and provide for a stable platform for solar panels and detector electronics.

Figure 1:
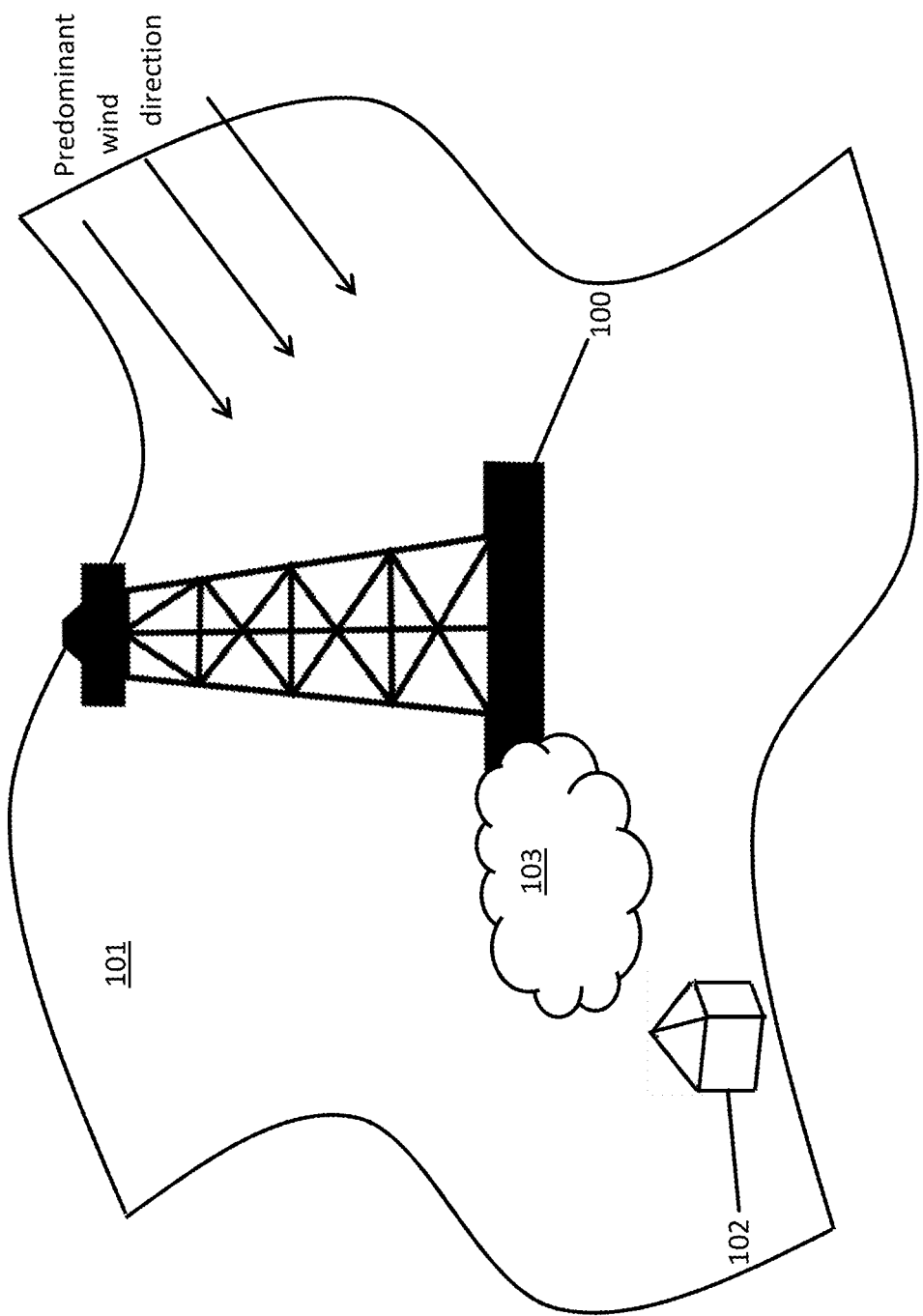
FIG. 1 is a perspective view of a hydro-fracking derrick and a gas sensing enclosure positioned down wind of the hydro-fracking derrick.

With reference to FIG. 1, a hydro-fracking derrick 100 is disposed for operation at a parcel of land 101 where the predominant wind direction is defined as shown by the arrows. A gas sensing enclosure 102 is disposed down wind of the hydro-fracking derrick 100 to sense a quantity of predefined types of gases in the atmosphere around the hydro-fracking derrick 100. The gas sensing enclosure 102 includes a coaxial stack of shells, protective membranes and sheathing as well as a gas sensor and associated circuitry and will be described in further detail below. While it is drawn down wind of the hydro-fracking derrick 100, it is to be understood that the gas sensing enclosure 102 need not be so positioned and may in fact be positioned at various locations around and at various distances from the hydro-fracking derrick 100.

During operations of the gas sensing enclosure 102 of FIG. 1, gases 103 that escape from the bore hole formed for the hydro-fracking derrick 100 are driven by wind to drift away from the bore hole and toward the gas sensing enclosure 102. The gases then infiltrate the gas sensing enclosure 102 and are analyzed by the gas sensor therein. Such infiltration can happen quickly and with little to no forewarning. Moreover, by the time the gases reach the gas sensing enclosure 102, the gases can be substantially diffuse. Therefore, the above-described aspects of the invention address the shortcomings of the prior art by configuring the gas sensor inside the gas sensing enclosure to be highly sensitive and fast acting. In addition, because the gas sensing enclosure 102 may sit alone in the parcel of land 101 for an extended period of time, the gas sensing enclosure 102 is able to survive in exposed atmospheric conditions, avoid infiltration by small animals and insects and has a power source that is long lasting and/or rechargeable.

With reference to FIG. 2, the gas sensing enclosure 102 includes a housing 110, shells 120, a gas sensor 130 and gas sensor controlling circuitry 140. The housing 110 includes a base 111, posts 112 (see FIGS. 6 and 7) extending upwardly from corners or sides of the base 111 and sidewalls 113. The sidewalls 113 extend upwardly from the base 111 and are or may be supported in that condition by the posts 112. In accordance with embodiments, the sidewalls 113 may include or be formed of screens 114.

With reference to FIGS. 3 and 4, the base 111 may have various regular or irregular shapes and sizes. For example, as shown in FIG. 3, the base 111 may be polygonal (e.g., square or rectangular) with posts 112 being positioned at its corners or sides. Alternatively, as shown in FIG. 4, the base 111 may be annular (e.g., circular or oval) with posts 112 arrayed at regular or irregular intervals about its circumference. In either case, the sidewalls 113 may be configured to be sufficiently rigid to stand on their own so that the posts 112 can be removed or discarded.

With reference back to FIG. 2, the housing 110 is formed to define an interior 115 and the shells 120 are arranged coaxially within the interior 115 of the housing 110. As shown in FIG. 2, the shells 120 include a lowermost shell 121, an uppermost shell 122, a lower intermediate shell 123 disposed at a first distance D1 above the lowermost shell 121 and an upper intermediate shell 124 disposed at a second distance D2 above the lower intermediate shell 123 and at a third distance D3 below the uppermost shell 122 although it is to be understood that as few as two shells (i.e., the lower intermediate shell 123 and the upper intermediate shell 124) may be provided.

In accordance with embodiments of the invention, it is to be understood that advantages of the four-shell configuration generally described herein are as follows. A first advantage is that the four-shell configuration collimates air flows through the gas sensing enclosure 102. A second advantage is that the four-shell configuration aids in providing ruggedness for the gas sensing enclosure 102 as a whole. A third advantage is that the lowermost shell 121 serves to thermally isolate and structurally protect the gas sensor controlling circuitry 140 while the uppermost shell 122 serves to shield the gas sensor 130 from solar radiation and to support solar panels disposed thereon.

Given the configuration of FIG. 2, the shells 120 form multiple substantially horizontal air flow pathways 150. That is, the lowermost shell 121 and the lower intermediate shell 123 form air flow pathway $150_1$ of thickness D1, the lower intermediate shell 123 and the upper intermediate shell 124 form air flow pathway $150_2$ of thickness D2 and the upper intermediate shell 124 and the uppermost shell 122 form air flow pathway $150_3$ of thickness D3. To this end, each of the shells 120 is configured to promote a smooth and possibly laminar flow of air through the air flow pathways 150. Thus, in accordance with embodiments, each of the shells 120 may be substantially flat or curved and, in some cases, pyramidal or frustoconical.

With reference to FIG. 5, the screens 114 may be configured to be gas and fluid permeable but impermeable to insects and small animals. Thus, while the insect 501 of FIG. 5 is turned away from the gas sensing enclosure 102, pathways 150 along which air can flow between consecutive or sequential shells 120 are permitted to be formed through the gas sensing enclosure a shown in FIGS. 2 and 5.

Figure 7:
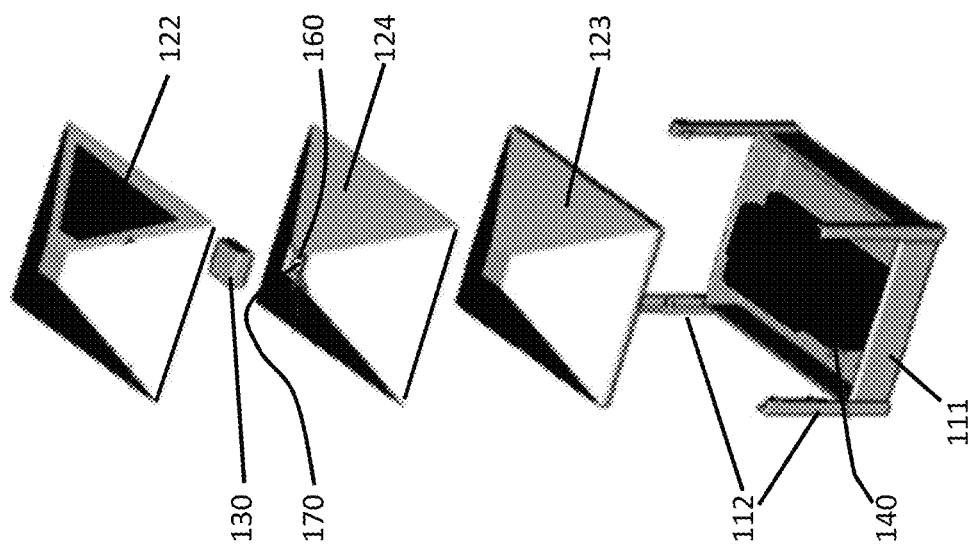
FIG. 7 is an exploded perspective view of the gas sensor enclosure of FIGS. 2 and 5.
Figure 6:
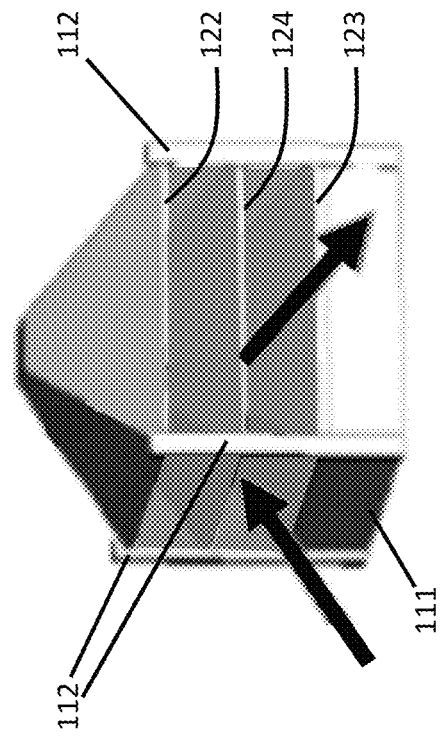
FIG. 6 is a perspective view of the gas sensor enclosure of FIG. 2.

With continued reference to FIG. 2 and with additional reference to FIGS. 6 and 7, where the shells 120 are pyramidal or frustoconical, the lowermost shell 121 may form a lower interior region 1210 with the base 111 and a perimeter of the lowermost shell 121 may be coupled to or proximate to the base 111. The uppermost shell 122 may form an uppermost portion of the gas sensing enclosure 100 and a perimeter of the uppermost shell 122 may be coupled to or supported on distal ends of the posts 112 (where applicable). The respective perimeters of the lower intermediate shell 122 and the upper intermediate shell 123 may be coupled to or supported on midpoints of the posts 112 (where applicable).

Figure 8:
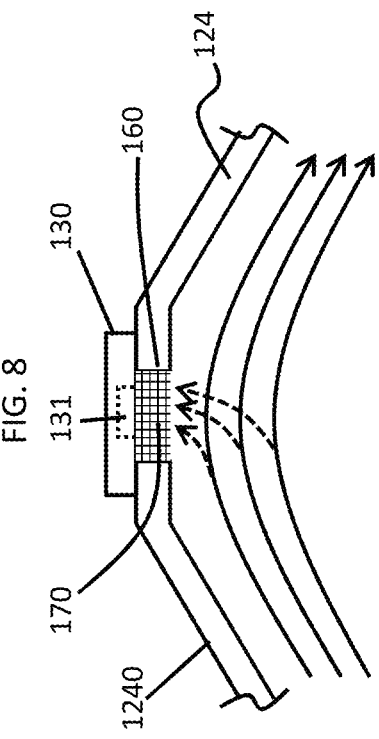
FIG. 8 is an enlarged side view of the larger encircled portion of the gas sensor enclosure of FIG. 2.

With reference to FIG. 8, the upper intermediate shell 124 may be formed to define an aperture 160 in a central region thereof and includes a gas permeable membrane 170 that is disposed within the aperture 160. In the case of the shells 120 being pyramidal or frustoconical, the central region would the region where the upper intermediate shell 123 is highest relative to the base. The gas permeable membrane 170 may be provided as a screen similar in pitch thickness to that of the screens 114 or as a fibrous membrane that could be formed of various materials (e.g., Goretex™). The gas sensor 130 is operably disposed on an upper surface 1240 of the upper intermediate shell 123 adjacent to the gas permeable membrane 170 and has a sensing portion 131 that is receptive of air flowing through the aperture 160 and the gas permeable membrane 170. The sensing portion 131 of the gas sensor 130 may be configured to have a volume that is small relative to an area of the aperture 160 and the gas permeable membrane 170 such that the gas sensor 130 has fast acting capability and is highly sensitive for various gas sensing applications.

In accordance with embodiments, the air flowing into the gas sensing enclosure 102 generally flows in a substantially horizontal direction along the ground. As this air flows through the gas sensing enclosure 102, a portion of the air flows into the gas sensor 130 via the aperture 160 and the gas permeable membrane 170 by osmosis or other similar phenomena.

In the cases in which the shells 120 are pyramidal or frustoconical, the air flow pathways 150 are formed such that the air flowing into the gas sensing enclosure 102 in the substantially horizontal direction along the ground is driven slightly upwardly by the "leading" side of the shells 120, is flattened out over the central portion of the shells 120 and then may be driven downwardly by the "trailing" side of the shells 120 (here, the "trailing" and "leading" sides are defined based on the current wind direction and could switch from moment to moment as wind directions change). The upward driving of the flowing air tends to increase a tendency of air to osmotically penetrate into and enter the gas sensor 130 via the aperture 160 and the gas permeable membrane 170.

With reference back to FIG. 2, the gas sensor controlling circuitry 140 may be operably disposed and arranged in the lower region 1210 between the base 111 and the lowermost shell 121. The gas sensor controlling circuitry 140 includes a printed circuit board (PCB) 141 and multiple electronic components 142 and may be configured to control various operations of the gas sensor 130. To this end, the gas sensor controlling circuitry 140 may be coupled to the gas sensor 130 wirelessly or by wired connections 143 that extend through-holes 144 in at least the lowermost shell 121 and the lower intermediate shell 123.

As shown in FIG. 2, the gas sensing enclosure 102 may further include at least one of a power source 180 and a solar panel 190. The power source 180 may be disposed on the PCB 141 along with the electronic components 142 of the gas sensor controlling circuitry 140 and may be provided as a battery or, more particularly, as a rechargeable battery. The solar panel 190 could be disposed on an exterior surface of the uppermost shell 122 and may be coupled to either or both of the gas sensor 130 and the gas sensor controlling circuitry 140 wirelessly or by wired connections 191 that extend through power supply through holes 192 in the appropriate shells 120.

With reference to FIG. 9, a method of assembling a gas sensing enclosure is provided. The method includes assembling a housing to include a base and sidewalls extending upwardly from the base 901. The sidewalls include screens that are gas and fluid permeable but insect impermeable. The method further includes arranging shells coaxially within the housing 902. The shells include a lowermost shell, an uppermost shell and an intermediate shell between the lowermost and uppermost shells. The intermediate shell includes a gas permeable membrane. The method further includes operably disposing a gas sensor on the intermediate shell adjacent to the gas permeable membrane 903 an d arranging gas sensor controlling circuitry between the base and the lowermost shell 904. Finally, the method includes coupling the gas sensor controlling circuitry to the gas sensor via through-holes in the lowermost and intermediate shells 905.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of assembling a gas sensing enclosure, the method comprising:
   assembling a housing to include a base and sidewalls extending upwardly from the base, the sidewalls comprising gas and fluid permeable screens that are impermeable to insects and small animals;
   arranging shells coaxially within the housing, the shells comprising a lowermost shell, an uppermost shell and an intermediate shell between the lowermost and uppermost shells, the intermediate shell comprising a gas permeable membrane;
   operably disposing a gas sensor on the intermediate shell adjacent to the gas permeable membrane;
   arranging gas sensor controlling circuitry between the base and the lowermost shell; and
   coupling the gas sensor controlling circuitry to the gas sensor via through-holes in the lowermost and intermediate shells.

2. The method according to claim 1, further comprising at least one of:
   disposing a power source in the gas sensor controlling circuitry; and
   coupling a solar panel to the gas sensor controlling circuitry.

3. The method according to claim 1, further comprising:
   arranging a solar panel on the uppermost shell; and
   coupling the solar panel to the gas sensor controlling circuitry via power supply through-holes in the uppermost, lowermost and intermediate shells.

4. The method according to claim 1, wherein the uppermost, lowermost and intermediate shells cooperatively form substantially horizontal flow paths across the housing.

5. The method according to claim 1, wherein:
   the intermediate shell comprises a lower intermediate shell and an upper intermediate shell,
   the upper intermediate shell comprising the gas permeable membrane and an upper surface on which the gas sensor is operably disposed.

6. The method according to claim 1, wherein the uppermost, lowermost and intermediate shells are pyramidal or frustoconical.

7. The method according to claim 1, wherein a volume of the gas sensor is small relative to an area of the gas permeable membrane.

8. The method according to claim 1, wherein the gas permeable membrane comprises a fibrous material.

* * * * *